United States Patent [19]

Kumura et al.

[11] Patent Number: 4,959,091
[45] Date of Patent: Sep. 25, 1990

[54] METHOD FOR INCREASING THE YIELD OF CROPS

[75] Inventors: Atsuhiko Kumura, Chiba; Ryuichi Ishii, Tokyo; Bing-Shan Luo, Chiba; Meiro Adachi; Kenji Hamada, both of Kanagawa; Fumio Fujita, Kanagawa, all of Japan

[73] Assignees: National Federation of Agricultural Co-Operative Associations; Nissan Chemical Industries, both of Tokyo, Japan

[21] Appl. No.: 777,746

[22] Filed: Sep. 19, 1985

[30] Foreign Application Priority Data

Sep. 20, 1984 [JP] Japan .................................. 59-195658
May 31, 1985 [JP] Japan .................................. 60-116537

[51] Int. Cl.$^5$ ............................................. A01N 43/22
[52] U.S. Cl. ............................................. 71/77; 71/88
[58] Field of Search ............................ 71/77, 88

[56] References Cited

U.S. PATENT DOCUMENTS 4,453,967  6/1984  Mori ........................................ 71/88

OTHER PUBLICATIONS

Takasuto et al., "Structure-Activity Relationship, etc.", (1983), CA 100: 153902d (1984).
Yopp et al., "Brassindide, a Growth-Promoting, etc.", (1981), CA 96: 64117b (1982).
Gregory, "Acceleration of Plant Growth, etc.", (1981), CA 95: 36959v (1981).
Wada et al., "Brassinelide and Homobrassinolide, etc.", (1981), CA 95: 2962a (1981).
Ishiguro et al., "Synthesis of Brassinolide, etc.", (1980), CA 94: 140032c (1981).
Grove et al., "Brassinolide a Plant, etc.", (1979), CA 92: 124868h (1980).

Primary Examiner—Glennon H. Hollrah
Assistant Examiner—Amehn A. Owens
Attorney, Agent, or Firm—Birch, Stewart, Kolasch & Birch

[57] ABSTRACT

The yield of crops (such as rice, wheat, corn, potato, soybean and other like major crops) can be increased according to a method wherein plants capable of yielding such crops are treated at a specific stage in their growing period with brassinolide, i.e. (2α,3α,22R,23R)-tetrahydroxy-24S-methyl-B-homo-7-oxa-5α-cholestan-6-one of the formula:

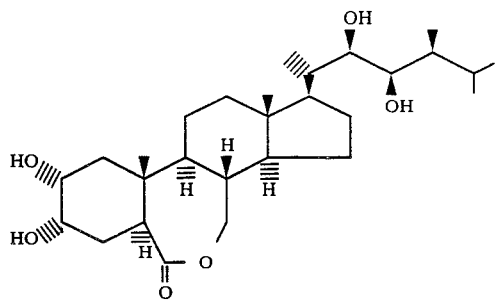

17 Claims, 9 Drawing Sheets

METHOD FOR INCREASING THE YIELD OF CROPS

BACKGROUND OF THE INVENTION

1. Field of the Invention

The present invention relates to a method for increasing the yield of crops and to a yield-increasing agent for crops used in the above method. More particularly, the present invention relates to a method for increasing the yield of crops by treating a plant capable of yielding a crop with brassinolide under specific conditions and to a yield-increasing agent for crops which contains brassinolide as an active ingredient thereof.

2. Description of the Prior Arts

Hitherto, a number of compounds have been found as substances capable of controlling growth and propagation of plants. Brassinolide, one of such compounds, is a steroidal plant-growth regulator isolated in 1979 from pollen of *Brassica napus* L. and determined as (2α,-3α,22R,23R)-tetrahydroxy-24S-methyl-B-homo-7-oxa-5α-cholestan-6-one having the following structure [Nature, Vol. 281, pp. 216-217(1979)]:

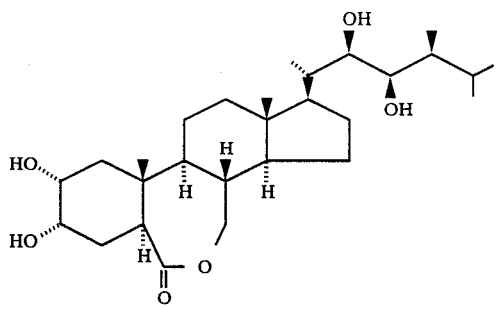

A great number of steroidal compounds are already known as hormones for animals and insects, but brassinolide is a steroidal compound found for the first time as a substance exhibiting physiological activities to plants. Thus, brassinolide is considered to be the 6th plant hormone subsequent to ethylene, auxin, gibberellin, cytokinin and abscicic acid, and is still being studied for its distribution in plants and its specific functions from the academic point of view.

Concerning the physiological effects of brassinolide to plants, various kinds of bioassay including the second internode elongation bioassay for kidney bean (*Phaseolus vulgaris*), rice lamina inclination bioassay and raphanus bioassay for radish (*Raphanus sativus*) have been made heretofore for comparison with other plant hormones [The Society for Chemical Regulation of Plants, Japan, 18(No. 1), 38–54(1983)]. As a result of gathering the previous reports, brassinolide is now being watched as possessing unique activities different from those seen in other plant hormones. Further, brassinolide exhibits a strong synergistic effect with auxin to various elongation bioassays for plants and also a synergistic effect with cytokinin to a propagation test for callus, thus proving significantly unique effects which will hardly be observed in using such known hormone alone. With respect to distribution of brassinolide in the plant kingdom, more than ten kinds of brassinolide analogues are already discovered widely in various plants in addition to brassinolide itself, and it is confirmed experimentally that these brassinolide compounds are contained widely in the higher plants such as rice (*Oryza sativa*), kidney bean (*Phaseolus vulgaris*), Chinese cabbage (*Brassica pekinensis*), tea (*Thea sinensis*), chestnut (*Castanea spp.*), hyacinth bean (*Dolichos lablab*), pine (*Pinus thunbergii*), cattail (*Typha latifolia*) and Distylium racemosum.

In the past, the effect of brassinolide to plants is known in the case of kidney bean wherein brassins as a crude extract from pollen of Rape (*Brassica napus* L.) is used [J. W. Mitchel and L. E. Gregory, Nature New Biology, 239, 253 (1972)] and in the case of radish, lettuce, kidney bean, pepper (*Piper nigrum*) and potato (*Solanum tuberosum*) wherein brassinosteroids as synthetic analogous compounds are used [Science, Vol. 212 (1981), 33–34]. The treatment for plants disclosed in these literatures comprises applying a lanolin paste to seedlings of kidney bean in case of the brassins and spraying an aqueous solution over seedlings in case of the brassinosteroids.

In Japanese Laid-open Patent Appln. No. Sho. 57-118503, there is disclosed 2R, 3S, 22S, 23S-tetrahydroxy-24S-ethyl-22S, 23S-5α-cholestan-6-one(22S, 23S-homobrassinolide), and their derivatives, one of the synthetic brassinolide analogues, which are explained therein as a substance effective for accelerating the growth of tomato (*Lycopersicon esculentum*), carrot (*Daucus carota*), mung bean (*Phaseolus aureus*), radish (*Raphanus sativus*), cucumber (*Cucumis sativus*) and azuki bean (*Phaseolus angularis*) by dipping seeds or seedlings of these plants in a solution of this 22S, 23S-homobrassinolide prior to soil culture. This reference further discloses that when tubers of potato, sweet potato seedlings, cuttings of branches of tea plant and seeds of tobacco are dipped in a solution of the 22S, 23S-homobrassinolide prior to cultivation, the 22S, 23S-homobrassinolide exhibits a growth-accelerating effect and that when the 22S, 23S-homobrassinolide is sprayed over fruit trees at the stage of anthesis, the diameter and weight of the fruits become larger. In Japanese Laid-open Patent Appln. No. Sho. 58-90578, there are also disclosed new synthetic 2R, 3S, 22R, 23R-tetrahydroxy-24S-ethyl-5α-cholestan-6-one and their derivatives (22R, 23R-homobrassinolide derivatives) and their use for accelerating the growth of various plants and improving the quality of agricultural products. In this reference, an elongation test for azuki bean is carried out by treating the seed with the 22R, 23R-homobrassinolide derivatives just before or after germination, but not concrete disclosure is given therein how the yield of crops is increased.

In general, plant-growth regulating agents are utilized by artificially controlling the growth of plants to achieve increased yields of crops, regulation of the amount of the agricultural products, improvement in quality, saving of work time and power, and regulation of harvest time. These plant-growth regulating agents are comprised chiefly of plant hormones, synthetic compounds possessing activities equivalent to such plant hormones and chemical substances having antagonistic effects to these. Recognized now as plant hormones are auxin, gibberellin, cytokinin, abscicic acid and ethylene. Many of the chemical substances actually employed for agricultural use a plant-growth regulating agents possess activity similar to those five plant hormones.

On the other hand, a great number of compounds are known which show physiological activity in vitro bioassay to plants, but the number of the compounds actually utilized for practical use are rather small. In ordinary in vitro bioassay, its experimental system is simplified with a view to detecting only a particular reaction, sharply minimizing the mutual effect with other organs and tissues. However, a plant body contains in its body a plurality of organs which are different in age and function and grow under their mutual actions to keep coordination. Thus, it is rather rare that the activity observed in vitro bioassay is reproduced exactly in whole plants. Further, strength of in vitro bioassay does not respond to importance in practical use. It is often observed that substances which exhibit similar equilivant activity in vitro bioassay may exhibit quite different activity to cultivated plants. In addition, it is also known that a quite different activity is often exhibited according to the concentration of the compound used. Furthermore, it is usual that the growing phenomena observed in applying the growth-accelerating agent to plants are different according to the sort and age of the plants. Thus, the growth reaction of plants to foreign substance varies according to the sort of plants and to the stage of their growth. In the extreme case, plants may often show a counter-reaction to such growth-increasing agent. It is quite impossible, therefore, to estimate growth-regulating activity on the basis of its in vitro bioassay. Thus, development of a new plant-growth regulating agent always encounters a great difficulty and is only possible by repeating "trial and error" tests to check its practical usefulness.

All of the prior art methods hitherto known relate to tests wherein a crude extract containing brassinolide or a synthetic brassinolide analogue is exclusively used for accelerating the growth of plants, but fail to disclose the effect of pure brassinolide itself on the growth of plants. Under these circumstances, therefore, there was still a great demand for developing a new method of using brassinolide for accelerating the growth of plants, especially for increasing the yield of crops.

BRIEF SUMMARY OF THE INVENTION

Accordingly, it is an object of the present invention to provide a method for increasing the yields of crops wherein brassinolide is used under specific conditions.

It is another object of the present invention to provide a yield-increasing agent for crops which contains brassinolide.

It is still another object of the present invention to provide the use of brassinolide for treating a plant capable of yielding a crop at a specific stage in its growing period.

Other and further objects, features and advantages of the present invention will be apparent more fully from the following description.

Since the discovery of brassinolide, a number of synthetic brassinolide analogues having structures similar to brassinolide have been developed and tested for various plants. Even if such synthetically similar compound exhibits a high plant-growth increasing activity at the level of in vitro bioassay, such compound would not be always effective for whole plants and would usually exhibit somewhat different activity according to the sort and age of plants, methods for treatment and the concentrations used. This will apply to the case of brassinolide itself. Thus in order to utilize only a specific activity among the various plant-physiological activities of brassinolide, a method for the treatment of plants with brassinolide has to be investigated for every plant. Standing on the above viewpoint, the present inventors have carefully paid their attention to the yield-increasing effect among the various activities exhibited by brassinolide and studied a method for the treatment with brassinolide for individual plants to examine the strength of the effect in connections with other related factors such as the time of application, concentration, etc. As a result of such extensive study it has now been found that the yield of main crops such as wheat, rice, corn, soybean and potato can be increased remarkably by applying a specific treatment with brassinolide to plants capable of yielding these main crops at a specific stage in their growing period. The conditions for treating these plants with brassinolide are strictly critical. Thus, the conditions for the treatment are quite inherent to the individual plants so that the yield-increasing effect of brassinolide cannot be expected at all and, in the extreme case, adverse effects may be incurred if the conditions inherent to particular plants are changed. Such conditions involve a combination of the concentration of brassinolide, the method of treatment and the time of application of brassinolide to particular plants and would not be anticipated at all even by those skilled in the art.

In accordance with one aspect of the present invention, therefore, there is provided a method for increasing the yield of crops, characterized in that a plant capable of yielding a crop is treated at a specific stage in its growing period with (2α,3α,22R,23R)-tetrahydroxy-24S-methyl-B-homo-7-oxa-5α-cholestan-6-one of the formula I:

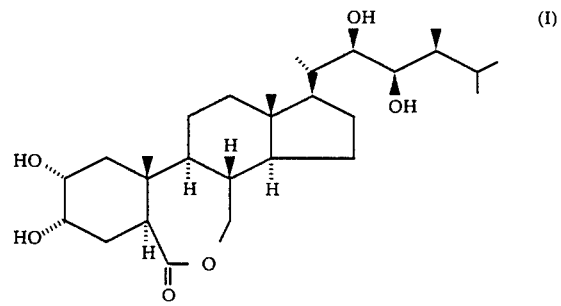

In accordance with another aspect of the present invention, there is provided a yield-increasing agent for crops which contains the compound of the formula I above as an active ingredient.

In accordance with still another aspect of the present invention, there is provided the use of the compound of the formula I for increasing the yield of crops.

DETAILED DESCRIPTION OF THE INVENTION

In the method of the present invention, it is important that plants capable of yielding crops are treated with brassinolide at a specific concentration and at a specific stage in their growing period. This specific stage in growing period is inherent to individual plants. By the term "growing period" referred to herein is meant a period normally from germination to ripening of crops in the form of grains, seeds, fruits or tubers. In certain cases, the term "growing period" involves a plant in the state of seed, grain or tuber. According to the method of this invention, therefore, a plant capable of yielding a crop is treated with brassinolide at a specific concentration at a certain stage in the growing period of the plant from the state of seed (grain) or tuber prior to germination to the state of ripened seed (grain), fruit or tuber.

Thus, for example, the state of germination, seedling, tillering or branching, emergence of ear and flowering are involved as intermediate stages of the above growing period.

Brassinolide used in the present invention is a crystalline substance soluble in organic solvents such as ethanol and acetone but sparingly soluble in water and can be synthesized according to a method improving the method of Mori et al. [Mori et al., Agric. Biol. Chem. 47(3), 663–664 (1983)] Brassinolide is usually employed in the form of a liquid formulation as a stock solution, an emulsifiable concentrate or a solid (powder or granular) formulation as a water-dispersible agent. On actual use, these formulations are diluted with a sufficient amount of water to have a given concentration of brassinolide. It is also possible to prepare a brassinolide paste based on lanolin to apply brassinolide directly to a specific part of plant.

In the preparation of such liquid formulation, brassinolide is dissolved in or homogeneously mixed with an organic solvent containing, if necessary, an auxiliary agent such as a wetting agent. Illustrative as the organic solvent are, for example, alcohols such as methanol, ethanol or propanol, ketones such as acetone, methyl ethyl ketone or methyl isobutyl ketone, glycols such as ethylene glycol, propylene glycol or diglyme, esters such as ethyl acetate or butyl acetate, hemiethers such as ethylene glycol monomethyl ether, amides such as dimethylformamide or hexamethylphosphoramide, sulfones such as diethylsulfone, ethers such as dioxane or tetrahydrofuran and aliphatic or aromatic hydrocarbons such as hexane, toluene or xylene, and a mixture of these.

In the preparation of the solid preparation in the form of powder, tablets or granules, brassinolide is thoroughly mixed with a solid carrier such as clay, acid activated clay, bentonite, talc, diatomaceous earth or the like mineral material together with an auxiliary agent such as a wetting agent, a dispersing agent or an emulsifier.

In the preparation of the paste, brassinolide is mixed with vaselin, lanolin, petroleum jelly or the like waxy substance, if necessary, together with an auxiliary agent such as an extending agent or dispersing agent.

Examples of the auxiliary agent usually employed for improving the extending, permeating, dispersing, binding, wetting and suspending properties of the above various formulations included non-ionic surfactants such as polyoxyethylene alkylphenyl ethers, polyoxyethylene dodecyl ethers, polyalkyleneglycol alkyl ethers and polyoxyethylene resin acid esters; anionic surfactants such as sodium dinaphthylmethanedisulfonate, sodium ligninesulfonate and sodium dodecylbenzenesulfonate; and other additives such as paraffin and D-sorbitol.

The amount and concentration of brassinolide in these formulation can be adjusted according to the sort of plants to be treated, the sort of formulations, and the method for the treatment. In general, brassinolide is allowed to be present in such liquid or solid formulation in an amount of about 10–1000 ppm and the content of brassinolide in the formulation is finally adjusted on actual use to a concentration of about $10^{-1}$ ppm to $10^{-4}$ ppm by dilution of the formulation with water or an extending agent. It is a matter of course, however, that the final concentration of brassinolide may be varied within a wide range according to the purpose of treatment, the sort of plants to be treated, the method of treatments and other various factors.

The treatment of plants with brassinolide can be carried out in various manners known per se. In case plants are to be treated with brassinolide at the stage of their seeds or tubers, for example, they are normally dipped in a diluted aqueous solution, dispersion or emulsion of the brassinolide formulations for a given period of time at a given concentration. Alternatively, a paste formulation of brassinolide may be applied to the seeds or tubers by painting or the like means. When plants are to be treated with brassinolide at any stage of germination, seedling, branching or tillering, emergence of ears, flowering and ripening, the plants are preferably sprayed with an aqueous solution, dispersion or emulsion or brassinolide at a given concentration according to a usual spraying method. In this case, one or more of the above mentioned various auxiliary agents may advantageously be incorporated into the brassinolide solution, dispersion or emulsion used with a view to improving a part or all of the wetting and spreading property, penetrating ability, dispersibibility, depositing property, sticking property, suspensibility of the treating agent. The spraying operation itself can be carried out by using any type of spray devices, but an aerial low volume spray by an aircraft may preferably be adopted when the plants in a broader area are treated within a short period of time. The treatment with brassinolide can be carried out singly or in combination with one or more of other treatments such as herbicidal or pesticidal treatments. In such combination treatment, one or more of the other plant hormones, fertilizers, herbicides, sterilizing agents, insecticides, etc. may be added to the brassinolide formulations.

The present invention can more fully be understood from the following description in conjunction with the accompanying drawings in which:

FIGS. 1(A)–1(C) are graphs showing results of tests wherein wheat was treated with an aqueous solution of brassinolide having a given concentration at various growing stages of wheat.

FIGS. 2(A)–2(C) are graphs showing results of tests wherein wheat was treated with the solution of brassinolide having a given concentration after anthesis to check the weight per grain and the relation between the concentration of brassinolide on the grain-setting of a specific part of the wheat ear.

Figure 6A:
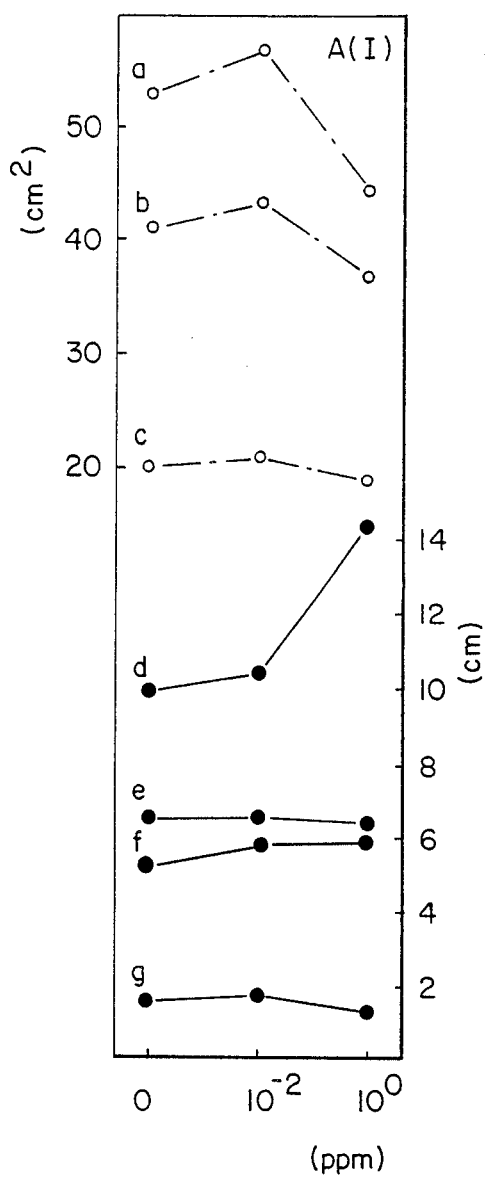
Figure 6B:
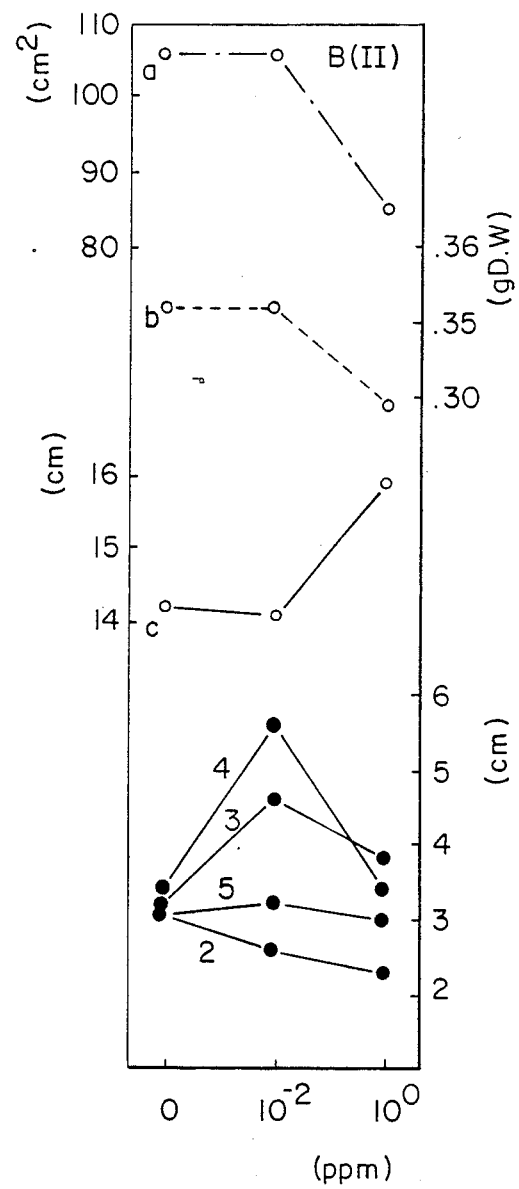

FIGS. 6(A) and 6(B) are graphs showing results of test wherein soybean was treated with an aqueous solution of brassinolide having a given concentration to check the effect of brassinolide on the growth of soybean at the early stages.

Figure 7A:
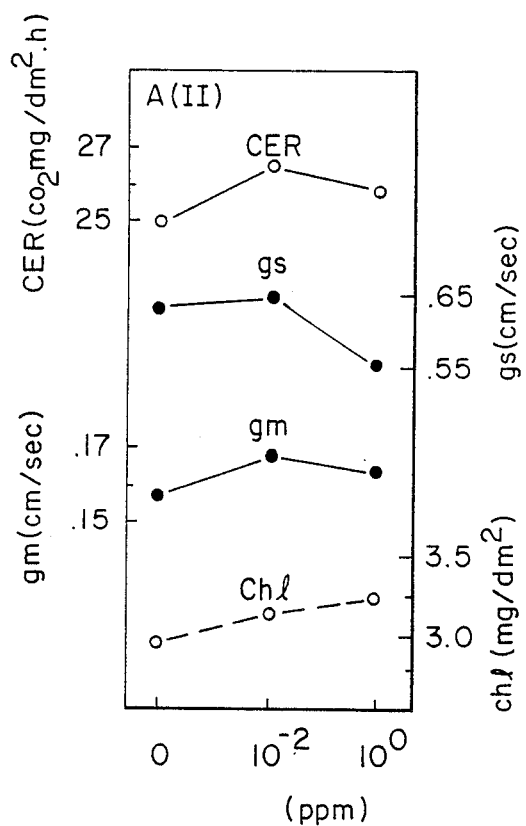
Figure 7B:
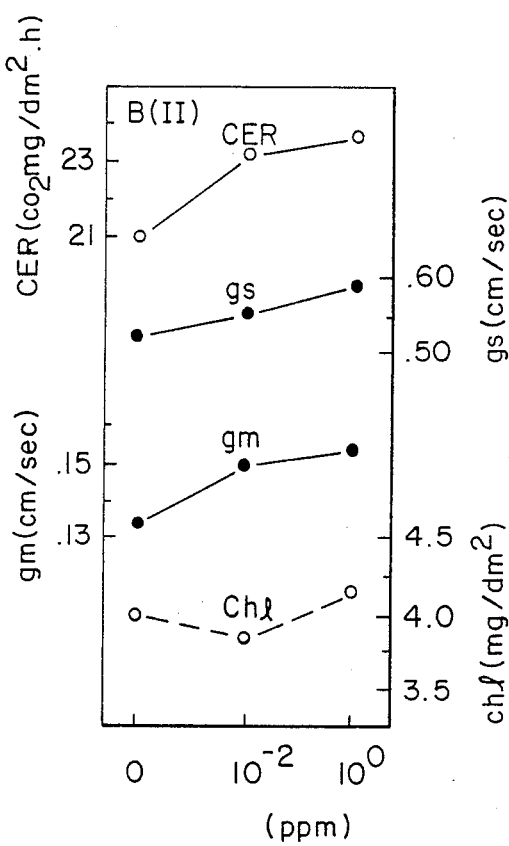

FIGS. 7(A) and 7(B) are graphs showing results of tests wherein soybean was treated with the solution of brassinolide at certain growing stages to check the effect of brassinolide on photosynthesis and the related factors.

Figure 8A:
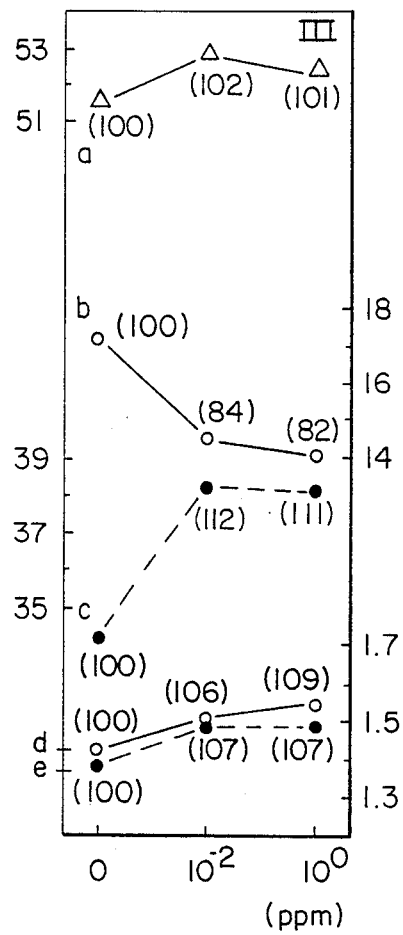
Figure 8B:
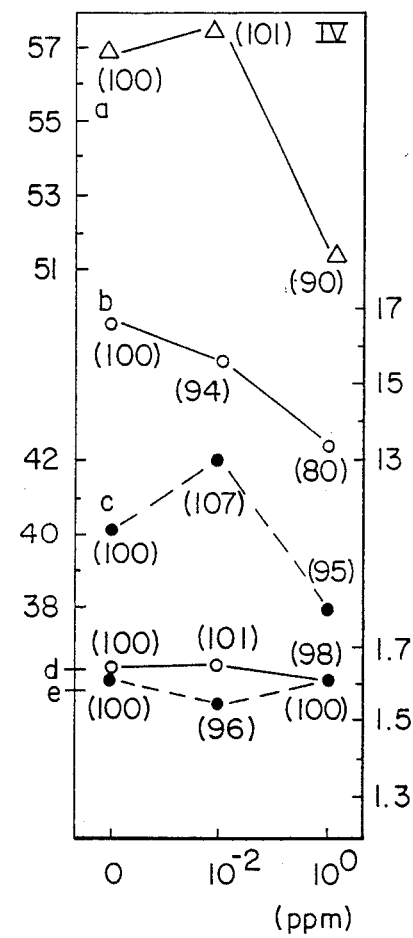

FIGS. 8(A) and 8(B) are graphs showing results of tests wherein soybean was treated with the solution of brassinolide at certain growing stages to check the effect of brassinolide on the seed-setting.

Figure 9A:
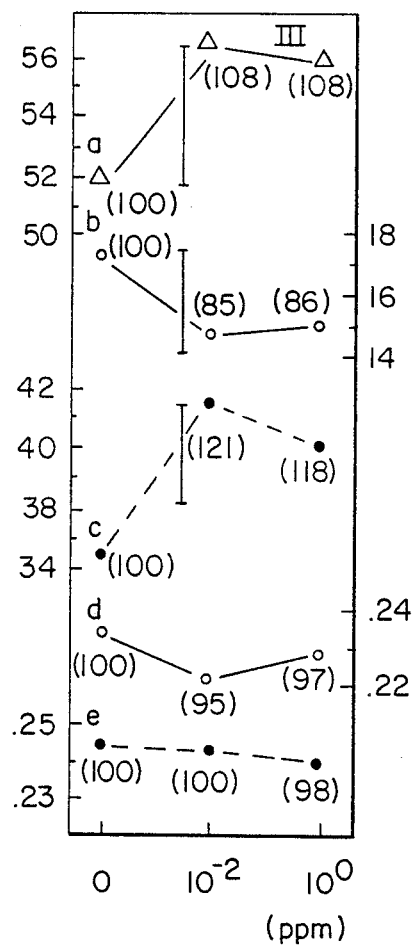
Figure 9B:
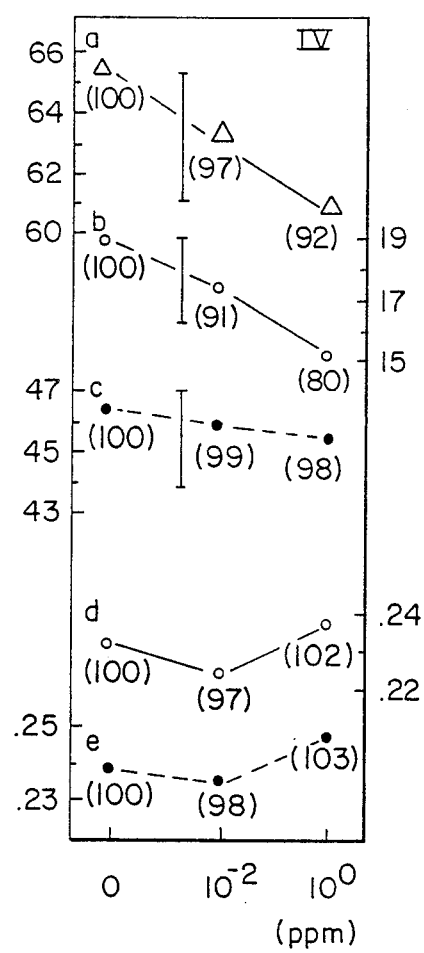

FIGS. 9(A) and 9(B) are graphs showing results of tests wherein soybean was treated with the solution of brassinolide to check its effect on the yield of soybean.

The method of the present invention can be carried out for increasing the yield of wheat as one of the gramineous crops. In this case, the yield-increasing effect of brassinolide is obviously exhibited when the wheat is treated with brassinolide at a specific concentration at the stage of seed prior to germination or in the flowering-ripening period. It has been found that when wheat is treated at its various growing stages with brassinolide to check its influence on the growing process of wheat, the ear weight of tillers and the ear weight of the main stem are significantly reduced in a plot where brassinolide has been sprayed from the beginning of tillering, as the concentration of brassinolide becomes higher. It has also been found that in a plot where brassinolide has been sprayed from the middle stage of spikelet differentiation, the ear weight of tillers is reduced but no influence is found in the ear weight of the main stem. In contrast, the ear weights of both tillers and the main stem were obviously increased as compared with the untreated control in a plot where brassinolide has been sprayed from the beginning of anthesis, thus resulting in increase in the percentage of grain-setting of florets located in the upper part of a spikelet. It has further been found that the treatment with brassinolide increases the weight per grain in each setting position of a particular spikelet sampled, the grain weight per spikelet and the total weight of grains of each spikelet and that the total grain weight becomes maximum by the treatment with brassinolide at a concentration of $10^{-2}$ ppm, showing increase by 10% in comparison with the untreated control. The treatment with brassinolide increases grain weight significantly especially in spikelets and grains located in the upper part of the ear. Thus, the treatment of wheat with brassinolide before anthesis rather gives bad influence on the ripening of grains and the yield of grains but the treatment of wheat with brassinolide during the period from anthesis to ripening serves to increase the percentage in grain-setting of florets located in the upper part of a spikelet and the weight of grains located in the upper part of a spikelet, thus bringing about an increased yield of grains. It is quite unforeseeable therefore that the percentage of grain-setting and the grain weight can be remarkably increased by treating wheat during the period from anthesis to ripening with brassinolide especially in the upper part of a spikelet where the percentage of grain-setting and the grain weight are usually low. It is also interesting that as will be evident from Example 2 the yield-increasing effect of brassinolide is exhibited also by treating the seed of wheat with brassinolide. The concentration of brassinolide varies according to the method of treatment and the sort of plants. In case of wheat, brassinolide is preferably sprayed over the whole plant and the concentration of brassinolide in this case is recommended to be about $10^{-1}$–$10^{-3}$ ppm. The number of the treatments with brassinolide varies according to the method of treatment, the sort of plants and the concentration used, but the treatment is usually carried out 1–5 times in case of spraying brassinolide at a concentration of $10^{-2}$ ppm.

An exact reason for the development of this yield-increasing effect is still unknown at the present stage, but it has been found, according to the present inventors' study, that the photosynthetic rate, stomatal conductance (gs) and mesophyll conductance (gm) are slightly promoted in young leaves but are rather inhibited in senescent leaves. It is considered that both of gs and gm participate in the change in photosynthetic rate by the treatment with brassinolide.

In case corn is treated with brassinolide, a significant yield-increasing effect is observed when an aqueous solution of brassinolide is sprayed from the early silking stage to ear and silk of the plant. As a result of the present inventors' study on the length and diameter of ear, kernel weight, column number of ear, kernel number per column and number of vacant kernels by spraying a solution of brassinolide having a given concentration onto ear and silk of corn at the early silking stage, it has been found that the treatment with brassinolide gave a significant influence especially on the length of unfertile tip portion of ear and the number of vacant kerners and increased the yield by 18–33% by weight as compared with the untreated control. As in the case of wheat, it is evident that the treatment with brassinolide contributes to increasing the rate of grain-setting of the floret located in the upper part of the ear where grain-setting is usually extremely poor.

In case of treating paddy rice with brassinolide, the yield-increasing effect is observed when the seed is dipped in an aqueous solution of brassinolide or when the paddy rice is treated with brassinolide at the maximum tillering stage. As a result of treating paddy rice at its several growing stages with brassinolide at several levels of concentration, it has been found that in a plot where the seed was dipped in the solution of brassinolide at a concentration of $10^{-2}$ ppm, the numbers of tillers and ears were increased by 7% and 15%, respectively, as compared with the untreated control so that the weight of unhulled rice was increased by 17% as shown in Table 4. However the 1000-kernel weight was almost unchanged and in a plot where the paddy rice was treated at the maximum tillering stage with brassinolide at concentrations of $10^{-2}$ ppm and $10^{-4}$ ppm by a foliage treatment, the number of grains per ear was increased by 11–13% as compared with the untreated control so that an average ear weight was increased by 5–7% (Table 5). However, a significant increase in the yield is not expected in case of treating the paddy rice with brassinolide at the young panicle formation stage and anthesis. Concerning the rate of increasing the number of grains in each part of the ear in the foliage treatment at the maximum tillering stage, the rate of increase in the upper 1st–4th rachises is within the range of 7–9% but that in the lower rachises is surprisingly 15–17%, thus showing the fact that brassinolide gives a strong influence on the grains located in the lower rachises where grains are usually not fully grown. This tendency is seen in the foliage treatment at the young panicle formation stage but the rate of increase is not so great as compared with the above case. Thus, the yield-increasing effect brought about by brassinolide sprayed at the maximum tillering stage results apparently from increase in the rate of grain-setting in the lower part of ears.

The method of the present invention can also be carried out for increasing the yield of soybean as one of pulse crops. As a result of treating soybean at its several growing stages with brassinolide at several levels of concentration, it has been found that brassinolide exhibits an accelerating effect on the elongation of epicotyls, internodes, petioles and branches. However, such effect varies according to the sort of organs and the concentration of brassinolide; the growth of leaf area was inhibited at a higher concentration of brassinolide. On the other hand, no significant influence is found on the node order of the first branching, number of branching, number of nodes on branches and node number of the main stem so that no accelerating effect is observed on the formation of organs. The treatment of soybean with brassinolide at the stage of unfolding of the 4th trifoliolate leaf and after fully expanding of the 4th trifoliolate leaf increase the photosynthetic rate. The amount of chlorophyll in the leaf of each leaf position on the stem is increased also by a consecutive treatment with brassinolide before or after flowering, thus showing a senescence-preventing activity to leaves. As a result of tests for examining the influence of brassinolide on the seed-setting and yield of soybean, a consecutive treatment with brassinolide before flowering increases the pod number of branch and the seed number per pod so that the total seed weight per plant can be increased. Contrary to this a consecutive treatment with brassinolide after flowering increases elongation of the branches and petioles to allow them to curve and rather decreases the rate of seed-setting and the yield. In case of soybean, therefore, the treatment in the period from the unfolding of the third trifoliolate leaf to the beginning of flowering increases the number of pods on branches and the seed number per pod, to show the yield-increasing effect for soybean. Consequently, the method for increasing the yield of pulse crops according to the present invention comprises treating a part of the plant such as flowers, leaves, stems or roots or the whole part of the plant with brassinolide in the period from the unfolding of the third trifoliolate leaf to the beginning of flowering. A proper device such as dipping, spraying, applying or the like means can be used for treating plants with brassinolide in the form of an aqueous solution, emulsion or dispersion to apply brassinolide to a particular part of the plants. The concentration of brassinolide varies according to the method of treatment or the sort of plants. In case of soybean, for example, it is preferable to spray an aqueous solution, dispersion or emulsion of brassinolide wholly over the plant at a concentration of about $10^{-1}$-$10^{-4}$ ppm. The number of the treatment varies according to the method of treatment, the sort of plants and the concentration of brassinolide used but is usually within the range of 1-5 times.

In case of the method of the present invention is applied to increase the yield of potato, it is preferable to dip divided tubers in an aqueous solution, dispersion or emulsion of brassinolide at a concentration of $10^{-3}$ to $10^{-5}$ ppm for 10-30 hours, thereby increasing the yield of tubers per plant by 10-20% as compared with the untreated control. An optimum concentration of brassinolide in this case is about $10^{-4}$ ppm. In a plot where an aqueous solution of brassinolide having a concentration of $10^{-4}$ ppm is sprayed two times over the whole plants, the number and weight of tubers per plant was almost equal to those of the untreated control, thus showing no increase in the yield of tubers. Thus, it is evident that the treatment of tubers with brassinolide prior to incorporation into soil is suitable for increasing the yield of potato.

As brassinolide is a natural substance which is contained widely in naturally occurring edible vegetables, it is a matter of course that no problem arises in connection with the safety and biodegradative property of brassinolide.

The present invention will now be illustrated in more detail by way of Formulation Examples and Examples wherein the term "BR treatment" meaning the treatment with brassinolide is used in Tables and in the descriptions relating to the various examination items.

FORMULATION EXAMPLE 1

(A Liquid Formulation)

A liquid formulation is prepared by dissolving 100 mg of brassinolide and 10 ml of Neoesterin (a wetting agent marketed by Kumiai Chemical Industry Co., Ltd., Japan) in 990 ml of ethyl alcohol and homogeneously mixing the solution. On actual use, the liquid formulation is diluted with water to a volume of 1,000-1,000,000 times.

FORMULATION EXAMPLE 2

(An Emulsifiable Concentrate)

An emulsifiable concentrate is prepared by homogeneously mixing the following ingredients:

| | |
|---|---|
| Brassinolide | 0.01 Part by weight |
| Dimethylformamide | 60 Parts by weight |
| Xylene | 30 Parts by weight |
| Nitten (a wetting agent marketed by Nissan Chemical Industries, Ltd.) | 10 Parts by weight |

FORMULATION EXAMPLE 3

(A Water-dispersible Powder)

A water-dispersible powder is prepared by thoroughly mixing and pulverizing the following ingredients:

| | |
|---|---|
| Brassinolide | 0.1 Part by weight |
| Diatomaceous Earth | 85 Parts by weight |
| Polyvinyl alcohol | 5 Parts by weight |
| Sodium dodecylbenzene-sulfonate | 9.9 Parts by weight |

FORMULATION EXAMPLE 4

(A Paste)

A paste is prepared by homogeneously mixing the following ingredients:

| | |
|---|---|
| Brassinolide | 0.001 Part by weight |
| Ethyl alcohol | 10 Parts by weight |
| Lanolin | 90 Parts by weight |

EXAMPLE 1

Using Asakaze wheat, a combination of tests was carried out according to the methods as shown in Table 1 to examine the effect of brassinolide applied to the wheat at various growing stages thereof.

A solution of 100 ppm brassinolide in ethyl alcohol was diluted with a 1:5000 aqueous solution of Neoesterin and the diluted solution was widely sprayed at a concentration of $10^{-4}$, $10^{-2}$ or $10^0$ ppm in a sufficient amount all over the wheat. The cultivation of the wheat was performed in a usual manner and a yield survey was made in Test Runs II, III and IV after harvest.

Figure 1A:
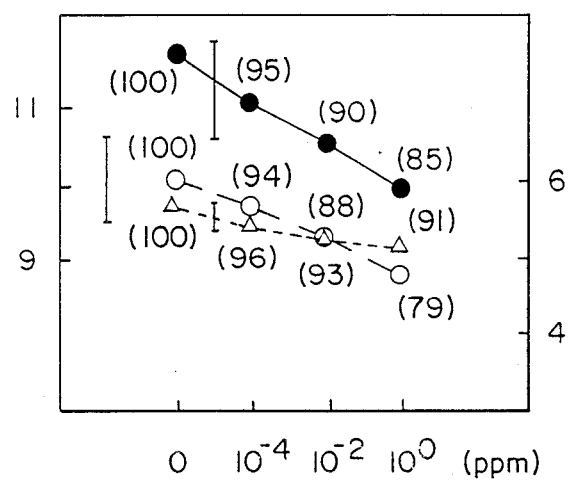
Figure 1B:
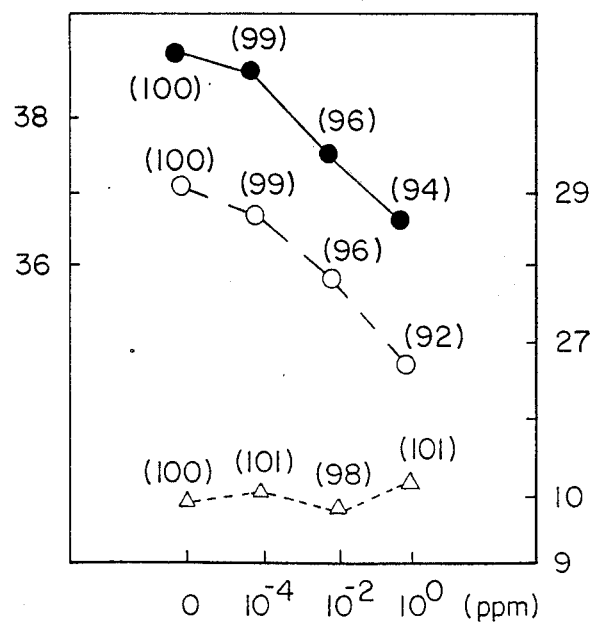
Figure 1C:
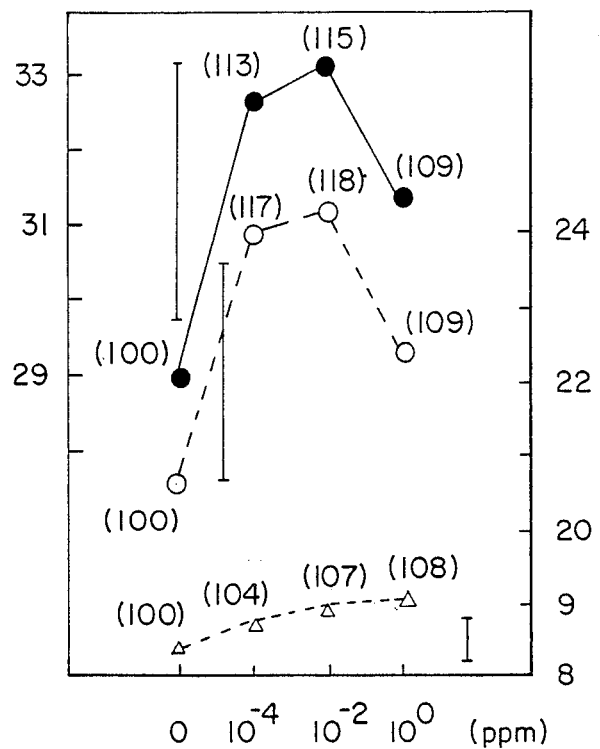

The survey was made for the five examination items, i.e. (1) the effect on germination and seedling growth, (2) the effect on tillering, (3) the effect on heading, (4) the effect on ear weight, and (5) the effect on grain-setting of ear on the main stem. Described below are results of the tests made according to the individual examination items. In addition, the results of the tests obtained in the test runs II, III and IV are shown in FIGS. 1(A), 1(B) and 1(C), respectively, and the results obtained in the test run IV are shown especially in FIGS. 2(A), 2(B) and 2(C) and FIGS. 3–5.

Results of the tests:

(1) The effect on germination and seedling growth

At a concentration of $10^{-2}$ or $10^0$ ppm, elongation of leaf sheath and roots was strongly inhibited but the number of roots was somewhat increased.

(2) The effect on tillering

TABLE 1

| | Testing method | |
|---|---|---|
| Test run | Method for cultivation | Method for BR treatment |
| I | (A) on a petri dish | dipping the seeds for 24 hours in the aqueous solution of BR at a given concentration |
| | (B) in a 2-liter beaker charged with soil Seeding depth: 5 cm | |
| II | sown a pot with the seeds on January 12th, 1984, the pot having been placed in a green house until March 3rd and then placed outdoors | treated 7 times with the aqueous solution of BR during the period from March 3rd (the beginning of tillering) to April 20th (the beginning of heading: April 29th) |
| III | sown a pot with the seeds on November 4th, 1983, the pot being placed outdoors | treated 7 times with the aqueous solution of BR during the period from March 3rd (the middle stage of spikelet defferentiation) to April 20th (the beginning of heading: April 27th) |
| IV | same as above | treated 5 times with the aqueous solution of BR during the period from May 2nd (the beginning of anthesis) to May 30th |

Remarks:
(1) "BR" means brassinolide
(2) In case of the test runs II, III and IV, the wheat was harvested on June 8th.

In the test runs II and III the tiller number was increased as the concentration of brassinolide became higher but, on the other hand, the percentage of productive stems was decreased so that the number of productive stems was decreased.

(3) The effect on heading

In the test run II the BR treatment showed the effect of retarding the heading time.

(4) The effect on ear weight

In the test run II, both ear weight of tillers and ear weight of the main stem were significantly decreased as the concentration of brassinolide became higher. In the test run III the ear weight of tillers was decreased by the BR treatment but no change was observed in the ear weight of the main stem. In the test run IV both ear weight of tillers and ear weight of the main stem were obviously increased by the BR treatment.

(5) The effect on the grain-setting of ear on the main stem

In the test run IV, the BR treatment served to increase the percentage of grain-setting of florets located in the upper part of a spikelet. Further, the BR treatment increased the weight per grain in each setting position of a particular spikelet sampled, the grain weight per spikelet in the upper, middle and lower parts of the ear, respectively, and the total weight of grains of each spikelet. The total grain weight became maximum with the BR treatment as a concentration of $10^{-2}$ ppm and was increased by 10% as compared with the untreated control. Increase in grain weight with the BR treatment was found significant especially in spikelets and grains located in the upper part of the ear.

In the graphs of FIGS. 1(A), 1(B) and 1(C) showing results of the test runs II, III and IV, respectively, the left-hand ordinate stands for the total ear weight per pot (in terms of g/pot) while the right-hand ordinate for the ear weight of tillers or the ear weight of the main stem per pot (in terms of g/pot). In each graph, the abscissa stands for the concentration of brassinolide used for the treatment (in terms of ppm), a solid line with black spots (— ●—● —) stands for the total ear weight, a broken line with white triangles (-Δ-Δ-) for the ear weight of the main stem, a broken line with white circles (-o-o-) for the ear weight of tillers, a vertical bar represents the least significant difference between means (p=0.05), and values in parentheses are relative values in case of the value in the untreated control being 100. FIGS. 1(A) and 1(B) apparently show that the total weight of the ears was rather decreased as the concentration of brassinolide became higher in the test runs II and III.

Figure 2A:
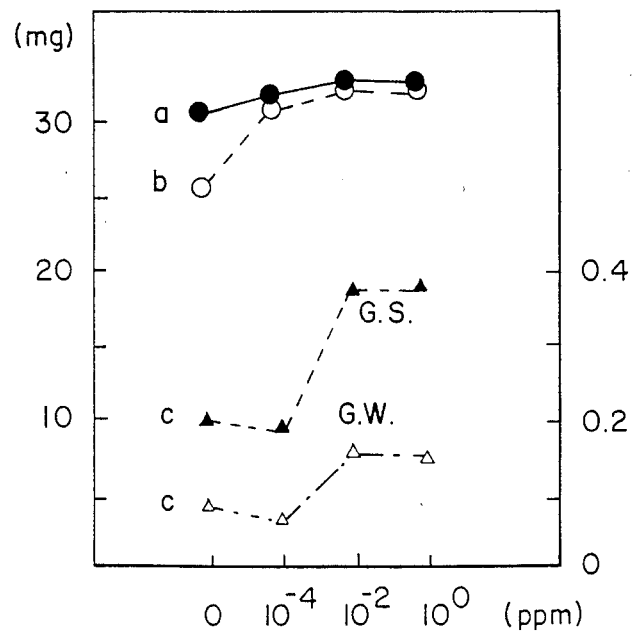
Figure 2B:
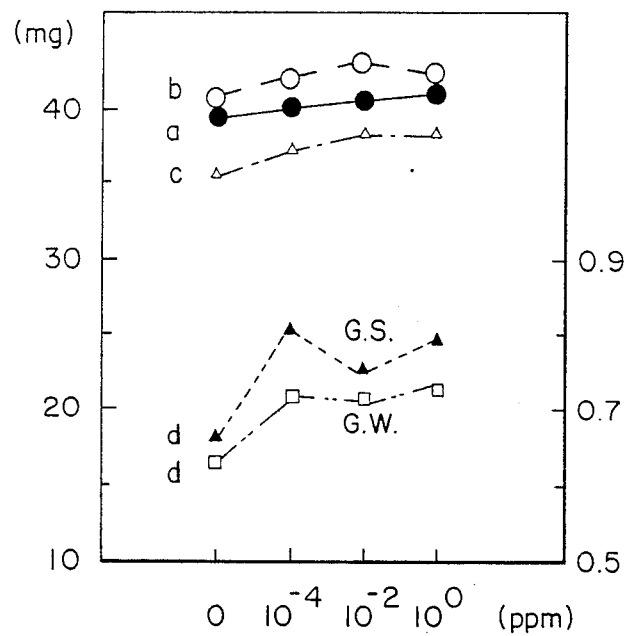
Figure 2C:
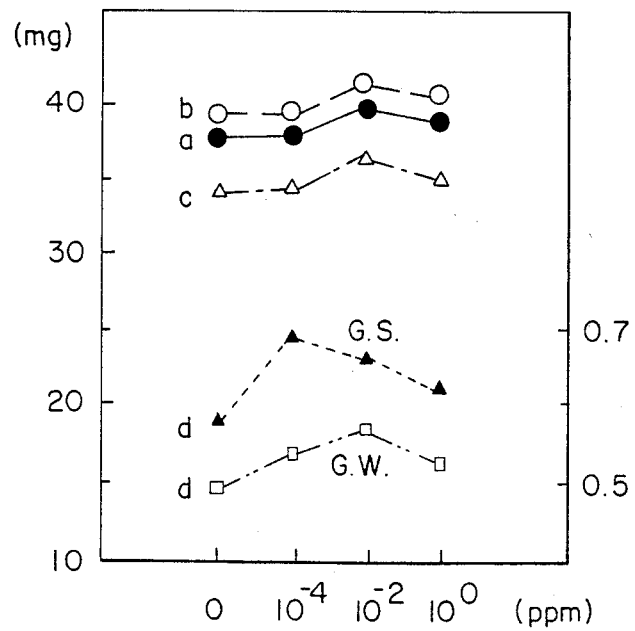

Among the graphs of FIGS. 2(A), 2(B), 2(C), 3, 4 and 5 showing results of the test for evaluating the effect of brassinolide on grain-setting of ear on the main stem in the test run IV, FIGS. 2(A), 2(B) and 2(C) show the weight per grain and the relation between the concentration of brassinolide in the treatment and the percentage of grain-setting of the topmost fertile floret in the spikelets located in the upper, middle and lower parts of the ear, respectively.

Throughout FIGS. 2(A), 2(B), 2(C), 3 and 4, the spikelet located in the upper part of the ear (the upper spikelet) means the third spikelet downwardly from the terminal spikelet while the spikelet located in the lower part of the ear (the lower spikelet) means the third spikelet upwardly from the basal spikelet. In FIGS. 2(A), 2(B) and 2(C), the position of grains in the spikelet was arbitrarily defined as follows: The bottommost position is defined as "a" and the positions "b", "c" and "d" are then successively defined upwardly from the bottommost position. In each of FIGS. 2(A), 2(B) and 2(C), the left-hand ordinate stands for the weight per grain (G.W. in terms of mg) and the right-hand ordinate for the percentage of grain-setting of the topmost fertile floret (G.S.) while the abscissa stands for the concentration of brassinolide in the treatment (in terms of ppm). In FIG. 2(A), the solid line a (— ●—● —) connects the plots standing for results in the grain located in the bottommost position of the upper spikelet treated at given concentrations of brassinolide, the broken line b (-o-o-) connects the plots standing for results in the grain in the position "b" of the upper spikelet treated at given concentrations of brassinolide and the line c (. . . ▲. . .▲ . . . ) with the notation "G.S." connects the plots standing for "G.S." of the grain in the position "c" in the upper spikelet treated at given concentrations of brassinolide, and the line c (-Δ-.-Δ) with the notation "G.W." connects the plots standing for "G.W." of the grain in the position "c" in the upper spikelet treated at given concentrations of brassinolide. In FIGS. 2(B) and 2(C), the lines a and b have the same meanings as given in FIGS. 2(A), the line c (-△-.-△-) connects the plots standing for results in the grain located in the position "c" in the middle or lower spikelet treated at given concentrations of brassinolide, the line d (... ▲ ... ▲ ...) of the grain in the position "d" in the middle or lower spikelet treated at given concentrations of brassinolide, and the line d (—□— ... —□—) with the notation "G.W." connects the plots standing for "G.W." of the grain in the position "d" in the middle or lower spikelet treated at given concentrations of brassinolide. In case of the upper spikelet, only 3 grains were involved therein and so the line d does not exist in FIG. 2(A) in contrast to FIG. 2(B) or 2(C) showing the result of 4 grains in the middle or lower spikelet.

Figure 3:
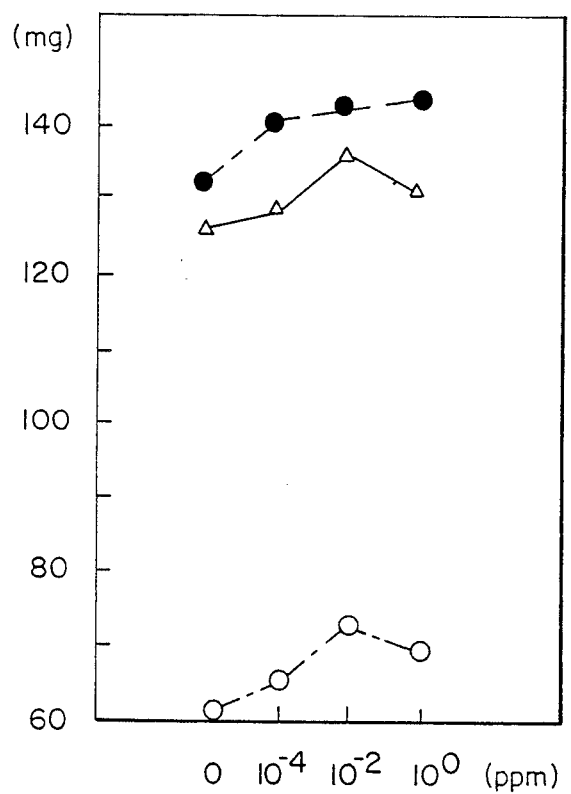
FIG. 3 is a graph showing a result of test wherein wheat was treated with the solution of brassinolide after anthesis to check the grain weight per spikelet.

FIG. 3 is a graph showing the grain weight per spikelet at given concentrations of brassinolide wherein the ordinate stands for the grain weight per spikelet (in terms of mg) while the abscissa for the concentration of brassinolide (in terms of ppm) and wherein the line (—●—●—) stands for the middle spikelet, the line (—△—△—) for the lower spikelet and the line (-o-.-o-) for the upper spikelet.

Figure 4:
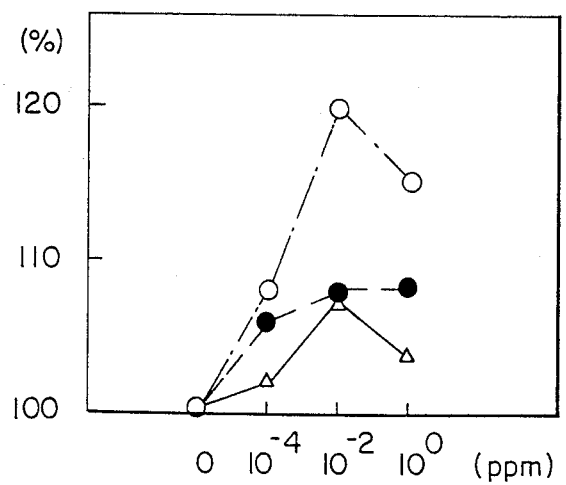
FIG. 4 is a graph showing a result of test wherein wheat was treated with the solution of brassinolide after anthesis to check the grain weight per spikelet.

FIG. 4 is a graph showing the grain weight per spikelet (in terms of percentage) at given concentrations of brassinolide wherein the ordinate stands for the grain weight per spikelet (in terms of percentage) while the abscissa for the concentration of brassinolide (in terms of ppm) and wherein the lines (-●-●—, -△-△- and -o-.-o-) have the same meanings as given in FIG. 3.

Figure 5:
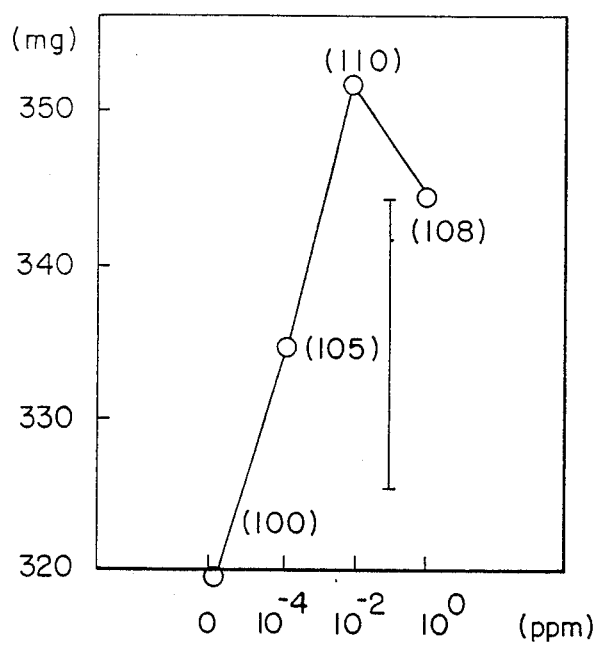
FIG. 5 is a graph showing a result of tests wherein wheat was treated with the solution of brassinolide after authesis to check the relation between the total grain weight of the specific spikelets and the concentration of brassinolide.

FIG. 5 is a graph showing the relation between the total grain weight of spikelets located in the upper, middle and lower parts of the ear and the concentration of brassinolide wherein the ordinate stands for the total grain weight (mg) of spikelets located in the upper, middle and lower parts (the upper, middle and lower spikelets) while the abscissa for the concentration of brassinolide (ppm). In FIG. 5, a vertical bar represents the least significant difference between means (p=0.05), and the values in parentheses are relative values in case of the value in the untreated control being 100.

EXAMPLE 2

Wheat seeds (Variety:Norin 61) were treated with brassinolide according to a dipping method wherein the seeds are dipped prior to germination in aqueous solutions of brassinolide having various concentrations ($10^{-1}$, $10^{-3}$ and $10^{-5}$ ppm) for 12 hours. A seed-disinfectant was added to the aqueous solutions at the same time. The seeds thus treated were washed with water, dried for 2 days at room temperature and used for the following test:

A cubic concrete pot having a size of 60 cm in length, 60 cm in width and 40 cm in depth was filled with a diluvial soil and sown with the wheat seeds in 3 rows with 30 seeds being sown in each row. The sown seeds were covered with the diluvial soil of 3 cm in depth. Just 7 months after the seeding, the total weight of ears and the total number of ears were measured and the weight per ear was calculated. A result of the test is shown in Table 2 below.

TABLE 2

| Agent | Concentration (ppm) | Total weight of ears | Total number of ears | Weight per ear |
| --- | --- | --- | --- | --- |
| Brassinolide | $10^{-1}$ | 116 | 101 | 115 |
| Brassinolide | $10^{-3}$ | 112 | 100 | 112 |

TABLE 2-continued

| Agent | Concentration (ppm) | Total weight of ears | Total number of ears | Weight per ear |
| --- | --- | --- | --- | --- |
| Control | — | 100 | 100 | 100 |

Remarks:
The results in the table are shown by relative values in case of the value in the untreated control being 100.

As is evident from Table 2, a significant increase in the total weight of ears and the weight per ear is found in case of the seeds treated with brassinolide.

EXAMPLE 3

To ear and silk of corn (*Zea mays*) cultivated in a green house an aqueous solution of brassinolide having a concentration of $10^{-4}$, $10^{-2}$ or $10^0$ was sprayed in a sufficient amount 1-3 times from the early silking stage. The test conditions were as follows:
Kind of corn: Honey Bantam
Test scale: 3 plants/plot
Soil: sandy loam (alluvial soil)
Interval of spraying: 1-3 times at intervals of a week from the early silking stage
Day of investigation: harvested and surveyed after the lapse of one week from the day of the third sprinkling
Examination items: length, diameter and weight of corn ear, length of an unfertile tip portion of ear, kernel number per column, column number of ear, number of vacant kernels and total kernel number Table 3 shows a result of the test. Below is a detailed information on the individual examination items.

(1) The effect on the ear length:
The treatment with brassinolide showed a tendency of increasing the ear length somewhat within the range of 0-15%.

(2) The effect on the diameter:
In each test area, the treatment with brassinolide showed a tendency of increasing the diameter of ear somewhat within the range of 2-14%.

(3) The effect on the length of an unfertile tip portion of ear:
In the plot where spraying of the aqueous brassinolide solution was carried out 2 times or 3 times, the length of an unfertile tip portion of ear was significantly shortened. In particular, in the plot where brassinolide was applied at a concentration of $10^0$ ppm, the length of an unfertile tip portion of the ear was shortened to 39-46% of the case observed in the untreated control. In the plot where brassinolide was applied at a concentration of $10^{-4}$ ppm, the length was shortened to 25-36%. Thus, the treatment with brassinolide obviously enhanced the ripening of the ear.

(4) The effect on the weight of ear:
In each plot, the weight of ear became greater than that in the untreated control. The treatment with brassinolide at concentrations of $10^0$ ppm, $10^{-2}$ ppm and $10^{-4}$ ppm gave 25%, 33% and 18% increases (an average value in case of the spraying by 1-3 times) respectively, in the weight of ear.

(5) The effect on the kernel number per column:
The treatment with brassinolide showed a tendency of increasing the kernel number per column (the number of kernels aligned vertically) somewhat within the range of 0-13%.

(6) The effect on the column number of the ear:

The treatment with brassinolide gave no influence on the column number (the number of kernels aligned horizontally of the ear.

(7) The effect on the number of vacant kernels:

A remarkable result was observed for the number of vacant kernels. In any of the test areas where brassinolide was applied at a concentration of $10^0$ ppm, the number of vacant kernels was less than 10% as compared with that in the untreated control area. In the test areas where the concentration of brassinolide was $10^{-2}$ ppm or $10^{-4}$ ppm, the number of vacant kernels was 11-24% or 15-35%, respectively.

(8) The effect on the total kernel number:

The treatment with brassinolide showed a tendency of increasing the total kernel number within the range of 10-25%.

The foregoing results apparently show that the treatment with brassinolide at the silking stage exhibited a tendency of increasing the yield in various items represented by this except the column number of the ear. In general, the effect on increasing the yield of corn is determined by increase or decrease in the length of an unfertile tip portion of the ear and in the number of vacant kernels. The treatment with brassinolide gave the most significant influence on these two examination items as compared with the untreated control. It is considered therefore that the effect on increasing the yield of corn by the treatment with brassinolide is exhibited by enhancing the ripening of kernels at the top portion which are usually hard to be ripened and decreasing the number of vacant kernels.

Day of harvest: Oct. 2nd

Examination items: plant height and number of tillers (on July 24th), weight of unhulled rice, 1000-kernel weight, and number of ears (after harvest).

Table 4 shows a result of the test. Below is a general evaluation on the individual examination items.

An average plant height was not so influenced by the treatment with brassinolide but the number of tillers was increased by 7% as compared with the case of the untreated control. The number of ears was increased in the treated plot by 15% as compared with that in the untreated control, but no change was observed in 1000-kernel weight. Thus, the weight of unhulled rice per unit test area was 17% greater than that in the untreated control.

TABLE 4

The yield-increasing effect of brassinolide on paddy rice in case of treating the seeds before hastening of germination

| Concentration of brassinolide ppm | Average plant height cm (%) | Number of tillers (%) | weight of unhulled rice g/3.3 m² (%) | 1000-Kernel weight g (%) | Number of ears Number/3.3 m² (%) |
|---|---|---|---|---|---|
| $10^{-2}$ | 67.8 (101) | 1275 (107) | 2018 (117) | 21.3 (99) | 910 (115) |
| Control | 67.1 (100) | 1192 (100) | 1725 (100) | 21.52 (100) | 791 (100) |

Remarks:
The values in parentheses are relative numbers (in percentage) in case of the values in the untreated control being 100.

TABLE 3

| Concentration of brassinolide (ppm) and Number of spraying | | Ear length (cm) | Diameter of Ear (cm) | Length of unfertile tip portion of ear (g) | Weight of Ear (g) | Kernel number per column | Column number of ear | Number of vacant kernels | Total kernel number |
|---|---|---|---|---|---|---|---|---|---|
| $10^0$ | 1 | 19.3 (107) | 4.3 (102) | 1.9 (68) | 196 (115) | 43 (108) | 12 (92) | 4 (7) | 512 (110) |
| | 2 | 18.8 (104) | 4.5 (107) | 1.1 (39) | 215 (126) | 41 (103) | 13 (100) | 2 (4) | 531 (114) |
| | 3 | 19.2 (107) | 4.5 (107) | 1.3 (46) | 226 (133) | 42 (105) | 14 (108) | 5 (9) | 583 (125) |
| $10^{-2}$ | 1 | 18.5 (103) | 4.7 (112) | 1.9 (68) | 216 (127) | 40 (100) | 14 (108) | 6 (11) | 554 (119) |
| | 2 | 19.2 (107) | 4.8 (114) | 2.0 (71) | 225 (132) | 41 (103) | 13 (100) | 10 (19) | 523 (112) |
| | 3 | 20.7 (115) | 4.6 (109) | 2.3 (82) | 236 (139) | 43 (108) | 13 (100) | 13 (24) | 546 (117) |
| $10^{-4}$ | 1 | 19.3 (107) | 4.5 (107) | 2.3 (82) | 220 (129) | 45 (113) | 12 (92) | 8 (15) | 532 (114) |
| | 2 | 18.7 (104) | 4.5 (107) | 0.7 (25) | 204 (120) | 44 (110) | 13 (100) | 16 (30) | 556 (119) |
| | 3 | 18.0 (100) | 4.4 (105) | 1.0 (36) | 181 (106) | 41 (103) | 13 (100) | 19 (35) | 514 (110) |
| Control | | 18.0 (100) | 4.2 (100) | 2.8 (100) | 170 (100) | 40 (100) | 13 (100) | 54 (100) | 466 (100) |

Remarks:
The values in parentheses are relative number (in terms of percentage) in case of the untreated control being 100.

EXAMPLE 4

This example illustrates the effect of brassinolide on increasing the yield of paddy rice in direct incorporation of paddy field with rice seeds. Seeds of paddy rice (variety: Musashikogane) were dipped before hastening of germination in an aqueous solution of brassinolide having a concentration of $10^{-2}$ ppm for 24 hours, germinated at 30° C., and then coated with Calper (Hodogaya Chemical Co., Ltd., Japan) in a ratio of 10:8 and directly incorporated into flooded paddy field. The test conditions used were as follows:

Day of sowing: May 11th 1984

Type of sowing: incorporation of the flood paddy field with the seeds at an interval of 1.5 cm in rows (an interval between the adjacent rows being 30 cm)

Depth of the incorporated seeds: 1 cm (covered with diluvial soil)

Quantity of the incorporated seeds: 500 g/are

Scale: 20 m²/plot (duplication/test)

EXAMPLE 5

Using a paddy rice (variety: Musashikogane), an aqueous solution of brassinolide having a concentration of $10^{-2}$ or $10^{-4}$ ppm was sprayed by a foliage treatment at certain growing stages, i.e. the maximum tillering, the young panicle formation stage and the anthesis stage, to check the influence of brassinolide and its application time on increase of yield. The test conditions employed were as follows:

Day of transplantation: May 17th 1984

Day of the beginning of heading: Aug. 12th

Day of harvest: Oct. 8th

Location of the test: Paddy field

Test scale: 10 m²/plot (duplication/test)

Spraying time:
 the maximum tillering stage (on June 27th)
 the young panicle formation stage (on July 20th)
 the anthesis (on Aug. 14th)

Amount of the solution sprayed: 15 liters/are

Examination items: yield, number of ears, average ear weight, 1000-kernel weight and number of grains per ear and rachis Twenty hills per plot were harvested to check the yield, the number of ears, the average ear weight, the 1000-kernel weight and the number of grains per ear. The number of grains was checked as per whole ear and as per the 1st–4th rachises counting downwardly from the ear top (the upper 1st–4th rachises) and rachises located in positions lower than the 4th rachis (the lower rachises), respectively.

A result of the test is shown in Tables 5 and 6 and briefly summarized below.

In the plot where the aqueous solution of brassinolide was sprayed wholly over the paddy rice at the maximum tillering stage, no change was observed in the number of ears but the number of grains per ear was increased by 11–13% at each concentration as compared with that in the untreated control so that an average ear weight of the hills in the treated plot was increased by 5–7%. Consequently, a yield-increasing effect as high as 10% by ear weight per 20 hills could be recognized at any concentration of brassinolide. In this case, the number of grains in the 1st–4th rachises counting downwardly from the ear top was 7–9% greater than that in the untreated control. Contrary to this, the number of grains in the lower rachises was 15–17% greater than that in the untreated control, thus showing a tendency that the increasing rate become higher as the grains were located in the lower part of ears. In the test area where the spraying was carried out at the young panicle formation stage, the number of grains was increased by 9% in the rachis lower than the 4th rachis irrespective of the concentration of brassinolide as in the case of the plot where the spraying was carried out at the maximum tillering stage, but the number of grains was increased only by 2–3% in the upper 1st–4th rachises so that the number of grains per ear was increased by 5–6% as compared with that in the untreated control. As the 1000-kernel weight was slightly decreased to 98% of that in the untreated control area, however, the ear weight per 20 hills was almost equal to that in the untreated control. In the treated plot where the spraying was carried out at the anthesis, an average ear weight, the 1000-kernel weight and the number of grains were all equivalent to those in the untreated control, and no difference was found in the ear weight per 20 hills in both plots.

TABLE 5

The yield-increasing effect of brassinolide on paddy rice in case of treating the paddy rice therewith at its growing stage

| Spraying time | Concentration of brassinolide ppm | Yield (ear weight of 20 hills per plot) g (%) | Number of ears of 20 hills (%) | Average ear weight g (%) | 1000-kernel weight g (%) | Number of grains Per whole ear (%) | The upper 1st–4th rachises (%) | The lower rachises (%) |
|---|---|---|---|---|---|---|---|---|
| Maximum tillering stage | $10^{-2}$ | 1567 (110) | 994 (104) | 1.56 (105) | 24.6 (98) | 69.1 (113) | 36.8 (109) | 32.0 (117) |
|  | $10^{-4}$ | 1568 (110) | 975 (102) | 1.59 (107) | 24.8 (99) | 67.9 (111) | 36.2 (107) | 31.5 (115) |
| Young panicle formation stage | $10^{-2}$ | 1426 (100) | 927 (97) | 1.51 (102) | 24.5 (98) | 64.2 (105) | 34.4 (102) | 29.9 (109) |
|  | $10^{-4}$ | 1440 (101) | 947 (99) | 1.52 (102) | 24.5 (98) | 64.9 (106) | 34.8 (103) | 29.8 (109) |
| Anthesis | $10^{-2}$ | 1439 (101) | 974 (102) | 1.47 (99) | 24.7 (99) | 61.3 (100) | 34.1 (101) | 27.1 (99) |
|  | $10^{-4}$ | 1425 (100) | 946 (99) | 1.50 (101) | 24.8 (99) | 64.3 (105) | 34.8 (103) | 29.3 (107) |
| Control | — | 1425 (100) | 956 (100) | 1.49 (100) | 25.1 (100) | 61.2 (100) | 33.8 (100) | 27.4 (100) |

Remarks:
The values in parentheses are relative number (in terms of percentage) in case of the values in the untreated control being 100.

TABLE 6

Distribution of the ear weights of paddy rice treated with brassinolide
(Spraying at the maximum tillering stage)

(A)

| Concentration of BR (ppm) | Ear weight (g) | | | | | | | | |
|---|---|---|---|---|---|---|---|---|---|
|  | 0~0.75 | 0.75~1.0 | 1.0~1.25 | 1.25~1.5 | 1.5~1.75 | 1.75~2.0 | 2.0~2.25 | 2.25~2.5 | 2.5~ |
| $10^{-2}$ | 3.3 | 5.1 | 11.4 | 16.6 | 21.1 | 21.1 | 14.7 | 5.7 | 1.0 |
| $10^{-4}$ | 2.3 | 6.5 | 9.0 | 19.7 | 21.4 | 23.6 | 12.6 | 4.6 | 0.7 |
| Control | 3.5 | 8.1 | 15.4 | 20.4 | 24.3 | 18.4 | 6.5 | 2.7 | 1.2 |

(B)

| Concentration of BR (ppm) | Ear Weight (%) | | | | | | | |
|---|---|---|---|---|---|---|---|---|
|  | 0~0.75 | 0~1.0 | 0~1.25 | 0~1.5 | 0~1.75 | 0~2.0 | 0~2.25 | 0~2.5 |
| $10^{-2}$ | 3.3 | 8.4 | 19.8 | 36.4 | 57.5 | 78.6 | 93.3 | 99.0 |
| $10^{-4}$ | 2.3 | 8.8 | 17.8 | 37.5 | 58.9 | 82.1 | 94.7 | 99.3 |

TABLE 6-continued

Distribution of the ear weights of paddy rice
treated with brassinolide
(Spraying at the maximum tillering stage)

| Control | 3.5 | 11.6 | 27.0 | 47.4 | 71.7 | 90.1 | 96.6 | 99.3 |

Remarks:
(1) "BR" means brassinolide.
(2) In Table (A), each range is sectioned by 0.25 g.
(3) In Table (A), each value stands for "total ear weight" in terms of percentage belonging to a relevant weight range.
(4) In Table (B), each value stands for a total sum of the values belonging up to the relevant range in Table (A) in terms of percentage.

EXAMPLE 6

A plurality of pots charged with soil were incorporated with seeds of Soybean (variety: Enrei) and 2 or 3 plants of the soybean were allowed to exist per pot and subjected to a test under field conditions according to the testing method as shown in Table 7. A solution of brassinolide in an amount of 100 ppm in ethyl alcohol was diluted with a 1:5000 aqueous solution of Nitten and the diluted solution of brassinolide was sprayed at a concentration of $10^{-2}$ or $10^0$ ppm in a sufficient amount all over the soybean plants. The cultivation of the soybean was carried out in a usual manner and the location of each pot was changed every week.

A survey was made for each examination item in the test runs I–IV as described in Table 7. Shown below are results of the tests according to the individual examination items. In addition, the results of the tests obtained in the test runs I–IV are shown in Tables 8 and 9 and FIGS. 6–9.

TABLE 7

| Test run | Testing method | |
|---|---|---|
| | Method for BR treatment | Examination items |
| I | After germination, 3 plants per pot treated with BR over the consecutive two days at the stage of the primary leaf expanding. | Two weeks after the BR treatment, the growth of the plants were checked. |
| II | Seeding was made on June 15th and, after germination, 2 plants per pot of 1/5000 a. (are), were supplied with 2 g of a compound fertilizer (N, P2O5 and K2O in a ratio of 12:15:15) as a basic manure and treated with BR over the consecutive two days at unfolding of the 4th trifoliolate leaf and after the full expansion of the 4th trifoliolate leaf. | In the test area where the plants were treated with BR at unfolding of the 4th trifoliolate leaf, the plants were examined 10 days after the treatment for photosynthesis in the leaf and the related internal factors within the leaf and 20 days after the treatment for the growth of the plants. In the test area where the plants were treated with BR after the full expansion of the 4th trifoliolate leaf, the plants were examined on the next day of the treatment for photosynthesis in the leaf and the relative factors within the leaf. |
| III | Seeding was made on June 16th and 3 plants per pot of 1/2000 a.(are), were supplied with 8 g of a compound fertilizer (N, P2O5 and K2O in a ratio of 12:15:15) and 4 g of potassium magnesium sulfate (55% in ratio of K to Mg) and treated 4 times with BR at an interval of 6 days in the period from unfolding of the 3rd trifoliolate leaf to flowering. | The plants were harvested on October 3rd and a survey was made for dimension of plant part, yield components and seed weight. |
| IV | Seeded and fertilized in the same manner as in the test run III, and treated 7 times with BR at an interval of 6 days in the period from flowering to ripening. | Same as in the test run III. |

Remarks:
"BR" means brassinolide

TABLE 8

The influence of a consecutive BR treatment
on the growth of leaves and the chlorophyll content

| | | Factor | | | | | | | | |
|---|---|---|---|---|---|---|---|---|---|---|
| | | Leaf area (cm²) | | | Petiole length (cm) | | | Chl a + b (mg/cm²) | | |
| | Leaf | Concentration of BR | | | | | | | | |
| Test run | position on the stem | 0 | $10^{-2}$ | $10^0$ (ppm) | 0 | $10^{-2}$ | $10^0$ (ppm) | 0 | $10^{-2}$ | $10^0$ (ppm) |
| III | 3 [treated 4 times] | 114.0 (100) | 110.0 (96) | 96.6 (87) | 16.2 (100) | 16.4 (101) | 19.4 (120) | 3.0 (100) | 3.15 (105) | 3.22 (107) |
| | 5 [treated 3 times] | 169.7 (100) | 164.2 (97) | 152.8 (90) | 19.8 (100) | 19.4 (98) | 21.6 (104) | 3.15 (100) | 3.59 (114) | 3.82 (121) |
| | 7 [treated 2 times] | 201.2 (100) | 199.4 (99) | 194.1 (95) | 23.2 (100) | 22.7 (98) | 22.7 (98) | 3.37 (100) | 3.42 (101) | 3.49 (104) |
| IV | 10 [treated | 218.9 | 211.6 | 203.7 | 26.8 | 27.5 | 29.0 | 3.70 | 3.83 | 3.84 |

TABLE 8-continued

The influence of a consecutive BR treatment
on the growth of leaves and the chlorophyll content

| Test run | Leaf position on the stem | Factor | | | | | | | | |
|---|---|---|---|---|---|---|---|---|---|---|
| | | Leaf area (cm$^2$) | | | Petiole length (cm) | | | Chl a + b (mg/cm$^2$) | | |
| | | Concentration of BR | | | | | | | | |
| | | 0 | 10$^{-2}$ | 10$^0$ (ppm) | 0 | 10$^{-2}$ | 10$^0$ (ppm) | 0 | 10$^{-2}$ | 10$^0$ (ppm) |
| | 6 times] | (100) | (96) | (93) | (100) | (103) | (110) | (100) | (104) | (104) |

Remarks:
(1) "BR" means brassinolide.
(2) Each value stands for an average value obtained by investigating 10 leaves.
(3) On measurement, the days after fully unfolding of each leaf listed under the column of "Leaf position of the stem" was as follows: 40 days in case of 3 (the third trifoliolate leaf), 36 days in case of 5 (the fifth trifoliolate leaf), 55 days in case of 7 (the seventh trifoliolate leaf) and 46 days in case of 10 (the tenth trifoliolate leaf).
(4) The values in parentheses are relative numbers (in terms of percentage) in case of the untreated control being 100.

TABLE 9

The influence of a consecutive BR treatment on the growth of soybean

| Test run | Concentration of BR (ppm) | Main stem | | | Node order of first branching | Number of branches (per plant) | Number of nodes on branches (per plant) | Length of branch (cm) | | | |
|---|---|---|---|---|---|---|---|---|---|---|---|
| | | stem length (cm) | Node number | Average node length (cm) | | | | 1 | 2 | 3 | 4 |
| III | 0 | 57.6 | 13.5 | 4.27 | 3.5 | 8.8 | 23.9 | 21.8 | 21.2 | 19.4 | 15.1 |
| (BR | 10$^{-2}$ | 57.7 | 13.5 | 4.27 | 3.4 | 8.6 | 25.2 | 25.5 | 26.1 | 19.9 | 15.4 |
| treatment before flowering) | 10$^0$ | 63.2 | 13.6 | 4.65 | 3.1 | 8.9 | 25.8 | 22.2 | 21.6 | 18.2 | 13.5 |
| IV | 0 | 58.9 | 13.4 | 4.40 | 3.5 | 8.6 | 24.9 | 27.7 | 28.0 | 19.7 | 13.7 |
| (BR | 10$^{-2}$ | 59.5 | 13.6 | 4.38 | 3.6 | 8.6 | 25.1 | 31.0 | 29.7 | 20.0 | 13.9 |
| treatment after flowering) | 10$^0$ | 60.0 | 13.5 | 4.44 | 3.2 | 8.7 | 25.9 | 29.9 | 30.7 | 24.2 | 19.7 |

Remarks:
(1) "BR" means brassinolide.
(2) Each value stands for an average value obtained by investigating 8 pots per treatment, each pot having 3 plants.
(3) In the column standing for length of branch, the numberals 1, 2, 3 and 4 mean the 1st, 2nd, 3rd and 4th branches, respectively.

Results of the tests:

1. The influence of the BR treatment on the growth of soybean:

According to the methods of the test runs I-IV, soybean was treated at several stages of growing with brassinolide to ascertain the effect of brassinolide at each stage of the growth of soybean.

(1) The BR treatment at the young seedling stage (during the period of the primary leaf expanding) (the test run I):

At a concentration of 10$^0$ ppm, elongation of the epicotyl was accelerated by 43% as compared with the case of the untreated control, but expansion of the primary leaf and the first trifoliolate leaf was inhibited by 11-14%. At a concentration of 10$^{-2}$ ppm, a slightly accelerating effect was observed in the growth of each organ but no significant influence was considered in this respect.

(2) The BR treatment at the seedling stage (at the stage of unfolding the fourth trifoliolate leaf) (the test run II):

(a) Growth of stem: At a concentration of 10$^{-2}$ ppm, elongation of the third internode (at the middle of the rapid elongation stage) and the fourth internode (at the beginning of the rapid elongation stage) was accelerated by 45% and 65%, respectively, as compared with the case of the untreated control. By the BR treatment, elongation of the second internode (at the end of elongation) was promptly stopped. At a concentration of 10$^0$ ppm, an accelerating effect on elongation of internodes at the middle of the elongation stage became weaker as compared with the case at a concentration of 10$^{-2}$ ppm, and an inhibitory effect on elongation of internodes at the end of the elongation stage became rather strong.

(b) Growth of leaves: In case of the BR treatment at a concentration of 10$^{-2}$ ppm, no significant influence was observed on the leaf area, dry weight and petiole length of the fourth trifoliolate leaf, but the BR treatment at a concentration of 10$^0$ ppm gave a significant influence on these factors. At the concentration of 10$^0$ ppm, the leaf area and the dry weight of the fourth trifoliolate leaf were both decreased by 19% as compared with the untreated control, but the petiole length became longer by 12%.

(3) The concecutive BR treatment during the period from the unfolding of the third trifoliolate leaf to the beginning of flowering stage (the test run III):

In case of a consecutive BR treatment at a concentration of 10$^0$ ppm, the leaf area became smaller while the petiole length became longer as shown in Table 8. The test run III was similar in this respect to the test runs I and II. No significant influence of the BR treatment was found on the other dimensions of plant parts as shown in Table 9. The BR treatment scarcely gave influence on the node order of first branching, the number of branches, the number of nodes on branches and the number of nodes on the main stem.

(4) The consecutive BR treatment during the period from the beginning of the flowering to the ripening (the test run IV):

A result of this test was almost same as that in the test run III.

2. The influence of the BR treatment on photosynthesis and matter production:

(1) The BR treatment before unfolding of the fourth trifoliolate leaf.

When the BR treatment was carried out at the stage of unfolding the fourth trifoliolate leaf and the measurement was made 10 days after the treatment, the photosynthetic rate (CER) was somewhat increased. Both chlorophyll content (Chl a+b) and mesophyll conductance (gm) were also increased slightly, but the stomatal conductance (gs) was not changed by the BR treatment at a concentration of $10^{-2}$ ppm and was reduced by 12% by the BR treatment at a concentration of $10^0$ ppm as compared with the untreated control.

(2) The BR treatment after fully expansion of the fourth trifoliolate leaf:

When the BR treatment was carried out after full expansion of the fourth trifoliolate leaf and the measurement was made on the next day of the treatment, the photosynthetic rate was enhanced by 10% at a concentration of $10^{-2}$ ppm and by 13% at a concentration of $10^0$ ppm as compared with the untreated control. In case of "gm" and "gs", the values were also slightly greater than those of the untreated control. No change was found in the chlorophyll content measured 10 days after the BR treatment.

When the BR treatment was continued before or after flowering, the chlorophyll content in leaves was slightly increased in all treated plots, thus exhibiting the effect of preventing the senescene of leaves as shown in Table 9.

3. The influence of the BR treatment on pod-setting, seed-setting and yield:

(1) The influence on pod-setting and seed-setting:

In case the soybean plants were treated consecutively with brassinolide before flowering (the test run III), no difference was found in total pod number between the treated plants and the untreated control, but the ratio in pod number of the branches to the main stem was significantly changed. By the BR treatment the pod number of the main stem was decreased by 16-18% as compared with the untreated control, but contrary to this, the pod number of the branches was increased by 12%. It was also recognized that the seed number per pod was increased by 6-9% by the BR treatment.

In the test run IV wherein the soybean plants were treated consecutively with brassinolide after flowering, the same tendency as in the treatment before flowering (the test run III) was seen with respect to the total pod number per plant and the ratio in pod number of the branches to the main stem in the treated plot at a concentration of $10^{-2}$ ppm. However, the difference in the ratio in pod number of the branches to the main stem became smaller. In the treated plot at a concentration of $10^0$ ppm, the pod numbers in the branches and the main stem per plant were decreased as compared with those of the untreated control, but the BR treatment gave no influence on the seed number per pod.

(2) The influence on yield:

In the test run III, the seed weight in the main stem per pot was decreased by 15% by the BR treatment as compared with the case of the untreated control, but the seed weight in branches was increased by 18-21%, thus increasing the total seed weight per pot by 8%. The weight per seed in the main stem was decreased by 3-5% by the BR treatment, but no influence on that was observed in the branches by the BR treatment.

In the test run IV, no change was found in the seed weight in branches per pot by the BR treatment but the seed weight in the main stem was lightened by 9% at a concentration of $10^{-2}$ ppm and by 20% at a concentration of $10^0$ ppm as compared with the cases of the untreated control so that the total seed weight per pot was decreased by 3% and 8%, respectively. No significant difference was found in the weight per seed in the seeds either produced in the branches or in the main stem, as compared with the untreated control.

Of the graphs of FIGS. 6(A) and 6(B) showing results of the test runs I and II, respectively, the graph of FIG. 6(A) shows a result, as average graphical data, of the test wherein soybean seedlings were treated twice with brassinolide during the period of the primary leaf expanding and 3 plants per pot (5 pots per treatment) were checked 2 weeks after the treatment and the graph of FIG. 6(B) shows a result, as average graphical data, of the test wherein soybean seedlings were treated twice with brassinolide at the stage of unfolding the 4th trifoliolate leaf and 2 plants per pot (5 pots per treatment) were checked 3 weeks after the treatment. In FIG. 6(A), the left-hand ordinate stands for leaf area (cm$^2$) while the right-hand ordinate for the length (cm) of various organs other than leaf. In the graph, lines with white circles stand for leaves while lines with black spots stand for organs other than leaf. The line a stands for the first trifoliolate leaf, the line b for the primary leaf and the line c for the second trifoliolate leaf. On the other hand, the line d stands for epicotyl, the line e for hypocotyl, the line f for the first internode and the line g for the second internode. In FIG. 6(B), the upper part of the left-hand ordinate stands for the leaf area in terms of cm$^2$ and the lower part for the petiole length in terms of cm while the upper part of the right-hand ordinate stands for the leaf weight (dry) in terms of g and the lower part for the internode length in terms of cm. The line a relates to the leaf area, the line b to the leaf weight (dry) and the line c to the petiole length. Regarding internode length, the numerals attached to the bold solid lines with black spots stand for the corresponding internodes; e.g. the line 2 stands for the second internode and the line 5 for the fifth internode. In each graph, the abscissa stands for the concentration of brassinolide used for the treatment (in terms of ppm). FIG. 6(A) apparently shows that expansion of the leaves was strongly inhibited and the elongation of epicotyl was strongly influenced by the treatment with brassinolide but no influence was observed in the growth of other organs. FIG. 6(B) shows that the area and dry weight of the leaf was decreased by the treatment with brassinolide but the petiole length was increased and a significant influence was found on the internode length.

In FIGS. 7(A) and 7(B), the upper part of the left-hand ordinate stands for the photosynthetic rate (CER) in terms of $CO_2$ mg/dm$^2$/hr and the lower part for the mesophyll conductance (gm) in terms of cm/sec, while the upper part of the right-hand ordinate stands for the stomatal conductance (gs) in terms of cm/sec and the lower part for the chlorophyll content (Chl) in terms of mg/dm$^2$. The abscissa in each graph stand for the concentration of brassinolide used for the treatment in terms of ppm. The graphs of FIGS. 7(A) and 7(B) show the influence of the treatment with brassinolide on the photosynthesis and its related factors of the fourth trifoliolate leaf. The graph of FIG. 7(A) shows a result, as average graphical data, of the plot wherein the soybean plant was treated twice with brassinolide at unfolding of the 4th trifoliolate leaf and 4 leaves per plot were checked 10 days after the treatment. The graph of FIG. 7(B) shows a result, as average graphical data, of the test wherein the soybean plant was treated twice with brassinolide after the full expansion of the 4th trifoliolate leaf and 4 leaves per plot were checked on the next day of the treatment.

FIGS. 8(A) and 8(B) are graphs showing the influence of the treatment with brassinolide on pod-setting and seed-setting of soybean. In case of FIG. 8(A), the graph shows a result, as average graphical data, of the test run III wherein the soybean plants were repeatedly treated with brassinolide (up to 4 times) before flowering and 3 plants per pot (8 pots per treatment) were checked after harvest. In case of FIG. 8(B), the graph shows a result, as average graphical data, of the test run IV wherein the soybean plants were treated up to 7 times with brassinolide after flowering and 3 plants per pot (8 pots per treatment) were checked after harvest. In FIGS. 8(A) and 8(B), the upper part of the left-hand ordinate stands for the total pod number per plant and the lower part for the pod number of branches per plant while the upper part of the right-hand ordinate stands for the pod number in the main stem per plant and the lower part for the seed number per pod. In each graph, the abscissa stands for the concentration of brassinolide used for the treatment (in terms of ppm) and the values in parentheses are relative values in case of the value in the untreated control being 100. For convenience's sake, the data on branches are shown by broken lines with black spot and the data on the main stem are shown by solid lines with white circles.

FIGS. 9(A) and 9(B) are graphs showing the influence of the treatment with brassinolide on the yield of soybean in the test runs III and IV, respectively. In graph of FIGS. 9(A) and 9(B), the upper part of the left-hand ordinate stands for the total seed weight (in terms of g/pot), the middle part for the seed weight of branches (in terms of g/pot) and the lower part for the weight per seed of branches (in terms of g/seed) while the upper part of the right-hand ordinate stands for the seed weight of the main stem (in terms of g/pot) and the lower part for the weight per seed of the main stem (in terms of g/seed). The results shown in FIGS. 9(A) and 9(B) are average data from 3 plants per pot (8 pots per treatment) and the values in parentheses are relative values in case of the value in the untreated control being 100. As in the case of FIGS. 8(A) and 8(B), the data on branches are shown by broken lines with black spots and the data on the main stem by solid lines with white circles. Vertical bar represents the least significant difference between means (p=0.05).

EXAMPLE 7

A tuber of potato (variety: Danshaku) was divided into 3 portions and each portion was dipped in an aqueous solution of brassinolide at a given concentration for 24 hours and incorporated into soil. In a plot where an aqueous solution of brassinolide was sprayed by foliage treatment, the solution at a concentration of $10^{-4}$ ppm was sprayed twice all over the plant at the stage of flowering. After harvest, the number of tubers per plant and the weight of tubers were investigated to evaluate the yield-increasing effect of brassinolide. The test conditions employed were as follows:

Day of incorporation: Mar. 8th 1985
Test place: crop field
Test scale: 60 cm × 4 m/plot (triplication)
Soil: Volcanic ash earth
Treatment: (Dipping treatment)
  One day before the incorporation, a tuber of potato divided into 3 portions was dipped in an aqueous solution of brassinolide at a concentration of $10^{-3}$, $10^{-4}$ or $10^{-5}$ ppm for 24 hours.
  (Foliage treatment)
    An aqueous solution of brassinolide having a concentration of $10^{-4}$ ppm was sprayed twice over the whole plant at the stage of flowering in a volume of 20 ml per plant.
Examination items: the number of tubers per plant and the weight of tubers (tubers in a size smaller than a table-tennis ball are omitted.)

A result of the test is shown in Table 10 below. Below is a general evaluation on the individual examination items.

In the plot where the tuber was subjected to the dipping treatment, the number of tubers was increased at each concentration by 17-20% as compared with the untreated control. On the other hand, an average weight of tuber was slightly increased in the plot where the concentration of brassinolide was $10^{-4}$ ppm, but the weight was slightly decreased in the plots where the concentration was $10^{-3}$ and $10^{-5}$ ppm. Thus, the yield per plant was increased in each of the plots where the concentration was $10^{-3}$, $10^4$ and $10^{-5}$ ppm in comparison with the untreated control, showing increase by 16%, 20% and 10%, respectively. It is considered therefore that the increase in the yield is chiefly ascribable to increase in the number of tubers per plant.

Contrary to the plots where the dipping treatment was made, an average weight of tuber was somewhat decreased in the plot where the foliage treatment was made although a tendency of slightly increasing the number of tubers per plant was observed. Consequently, the yield per plant in the plots where the foliage treatment was made was almost same as in the untreated control.

TABLE 10

| | | | | | | | |
|---|---|---|---|---|---|---|---|
| | | The effect of brassinolide on the increase in the yield of potato | | | | | |
| Treatment with brassinolide | Concentration of brassinolide (ppm) | Number of plants/ plot | Number of tubers | Yield/ plot (kg) | Number of tubers per plant | Average weight of tuber | Yield per plant (g) |
| Dipping treatment | $10^{-3}$ | 48 | 357 | 30.9 | 7.44 (120) | 86.6 (97) | 644 (116) |
| | $10^{-4}$ | 46 | 336 | 30.4 | 7.30 (118) | 90.5 (102) | 661 (120) |
| | $10^{-5}$ | 49 | 354 | 29.9 | 7.22 (117) | 84.5 (95) | 610 (110) |
| Foliage treatment | $10^{-4}$ | 48 | 308 | 26.9 | 6.42 (104) | 87.3 (98) | 560 (101) |

TABLE 10-continued

| | The effect of brassinolide on the increase in the yield of potato | | | | | | |
|---|---|---|---|---|---|---|---|
| Treatment with brassinolide | Concentration of brassinolide (ppm) | Number of plants/ plot | Number of tubers | Yield/ plot (kg) | Number of tubers per plant | Average weight of tuber | Yield per plant (g) |
| Control | — | 48 | 297 | 26.4 | 6.19 (100) | 88.9 (100) | 550 (100) |

Remarks:
(1) The values in parenthesis are relative values (in terms of percentage) in case of the untreated control being 100.
(2) In the untreated control, tubers were incorporated into soil without dipping.

It is understood that the preceding representative examples may be varied within the scope of the present specification both as to the sorts of plants and the treating conditions by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A method for increasing the yield of crops, which comprises treating
    gramineous crops during a flower ripening period with an effective amount of (2α, 3α, 22R, 23R)-tetrahyroxy-24S-methyl-B-homo-7-oxa-5α-chloestan-6-one of the formula I:

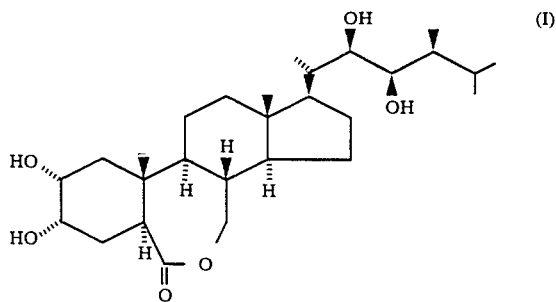

2. The method according to claim 1, wherein the amount of the compound of formula I is about $10^{-1}$ to $10^{-4}$ ppm.

3. The method according to claim 1, wherein said crops are treated by dipping, spraying or painting a paste containing an effective amount of the compound of formula I.

4. The method according to claim 1, wherein said crops are treated by spraying $10^{-1}$ to $10^{-3}$ ppm of the compound of formula I thereon.

5. The method according to claim 4, wherein said crops are treated 1–5 times at a concentration of $10^{-2}$ ppm.

6. The method according to claim 2, wherein the number of treatments is about 1–5 times.

7. The method according to claim 1, wherein the gramineous crops are selected from the group consisting of paddy rice, wheat, barley, rye and corn.

8. The method according to claim 1, wherein the gramineous crop is a wheat (Triticum aestivum).

9. The method according to claim 1, wherein the gramineous crop is a corn (Zea mays).

10. The method according to claim 1, wherein the gramineous crop is a paddy rice (Oryza sativa).

11. The method according to claim 9, wherein said treatment comprises spraying corn with an effective amount of the compound of formula I.

12. A method for increasing the yield of crops, which comprises treating pulse crops during the period from the emergence of the third trifoliate leaf to the initial stage of flowering with an effective amount of (2α, 3α, 22R, 23R)-tetrahydroxy-24S-methyl-B-homo-7-oxa-5α-chloestan-6-one of the formula I:

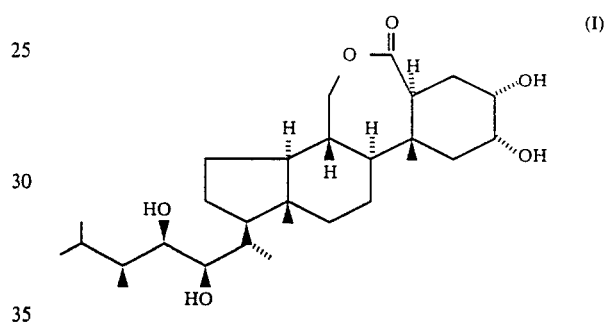

13. The method according to claim 12 wherein the pulse crop is soybean (Glycine max).

14. The method according to claim 12, wherein said treatment comprises spraying soybean with an effective amount of compound I.

15. A method for increasing the yield of crops which comprises treating potato in the form of whole or divided tuber prior to planting in the soil with an effective amount of (2α,3α,22R,23R)-tetrahydroxy-24S-methyl-B-homo-7-oxa-5α-chloestan-6-one of the formula I:

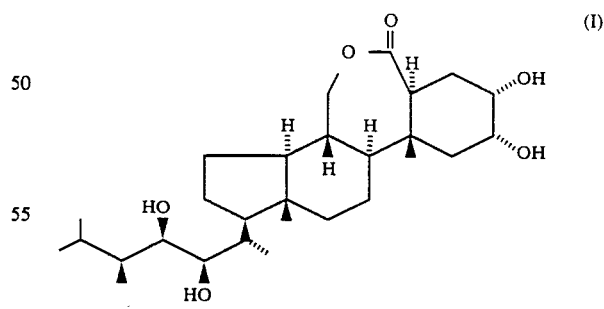

16. The method according to claim 15, further comprising, dipping tubers in an aqueous solution, dispersion or emulsion of $10^{-3}$ to $10^{-5}$ ppm of the compound of formula I for 10–30 hours.

17. The method according to claim 15, wherein said treatment comprises dipping potato in an effective amount of compound I.

* * * * *